United States Patent
Paudel et al.

(10) Patent No.: US 10,849,543 B2
(45) Date of Patent: Dec. 1, 2020

(54) FOCUS-BASED TAGGING OF SENSOR DATA

(71) Applicant: Ford Global Technologies, LLC, Dearborn, MI (US)

(72) Inventors: Shreyasha Paudel, Sunnyvale, CA (US); Jinesh Jain, Palo Alto, CA (US); Clifton Thomas, Palo Alto, CA (US)

(73) Assignee: FORD GLOBAL TECHNOLOGIES, LLC, Dearborn, MI (US)

(*) Notice: Subject to any disclaimer, the term of this patent is extended or adjusted under 35 U.S.C. 154(b) by 257 days.

(21) Appl. No.: 16/004,025

(22) Filed: Jun. 8, 2018

(65) Prior Publication Data
US 2019/0374151 A1     Dec. 12, 2019

(51) Int. Cl.
| | |
|---|---|
| G01C 21/36 | (2006.01) |
| A61B 5/18 | (2006.01) |
| B60W 40/09 | (2012.01) |
| G05D 1/00 | (2006.01) |
| A61B 5/00 | (2006.01) |
| A61B 5/16 | (2006.01) |

(52) U.S. Cl.
CPC ............... *A61B 5/18* (2013.01); *A61B 5/163* (2017.08); *A61B 5/7267* (2013.01); *B60W 40/09* (2013.01); *G05D 1/0088* (2013.01); *B60W 2420/52* (2013.01); *B60W 2540/30* (2013.01)

(58) Field of Classification Search
CPC ......... A61B 5/18; A61B 5/163; A61B 5/7267; B60W 40/09; B60W 2420/52; B60W 2540/30; G05D 1/0088
See application file for complete search history.

(56) References Cited

U.S. PATENT DOCUMENTS

| | | | |
|---|---|---|---|
| 8,384,534 B2 | 2/2013 | James | |
| 9,586,591 B1* | 3/2017 | Fields | B60K 35/00 |
| 9,791,286 B2 | 10/2017 | Di Censo | |
| 9,956,962 B2* | 5/2018 | Wacker | A61B 5/18 |
| 10,159,436 B2* | 12/2018 | Bieg | A61B 3/0025 |
| 2010/0033333 A1* | 2/2010 | Victor | A61B 5/1114 340/576 |
| 2012/0271484 A1* | 10/2012 | Feit | B60W 30/12 701/1 |

(Continued)

FOREIGN PATENT DOCUMENTS

WO     WO-201800037 A1     1/2018

OTHER PUBLICATIONS

Predicting the Driver's Focus of Attention: the DR(eye)VE Project.

*Primary Examiner* — Calvin Cheung
(74) *Attorney, Agent, or Firm* — David R. Stevens; Stevens Law Group (57) ABSTRACT

Data from sensors of a vehicle is captured along with data tracking a driver's gaze. The route traveled by the vehicle may also be captured. The driver's gaze is evaluated with respect to the sensor data to determine a feature the driver was focused on. A focus record is created for the feature. Focus records for many drivers may be aggregated to determine a frequency of observation of the feature. A machine learning model may be trained using the focus records to identify a region of interest for a given scenario in order to more quickly identify relevant hazards.

17 Claims, 5 Drawing Sheets

(56) References Cited

U.S. PATENT DOCUMENTS

| | | | |
|---|---|---|---|
| 2014/0139655 A1* | 5/2014 | Mimar | G08B 21/0476 348/77 |
| 2014/0199662 A1* | 7/2014 | Armitage | B60K 35/00 434/65 |
| 2014/0272810 A1* | 9/2014 | Fields | G09B 9/052 434/65 |
| 2014/0276090 A1* | 9/2014 | Breed | A61B 5/14546 600/473 |
| 2015/0339589 A1 | 11/2015 | Fisher | |
| 2016/0167672 A1* | 6/2016 | Krueger | A61B 5/7282 340/576 |
| 2016/0272215 A1* | 9/2016 | Laine | G08G 1/166 |
| 2017/0001648 A1 | 1/2017 | An | |
| 2018/0012085 A1 | 1/2018 | Blayvas | |
| 2018/0118219 A1* | 5/2018 | Hiei | B60W 50/14 |
| 2019/0031085 A1* | 1/2019 | Ba | G06N 5/047 |
| 2019/0147274 A1* | 5/2019 | Tanaka | B60W 40/09 701/36 |
| 2019/0156134 A1* | 5/2019 | Krishnan | A61B 5/225 |
| 2019/0213976 A1* | 7/2019 | Rakshit | B60K 37/02 |
| 2019/0246036 A1* | 8/2019 | Wu | H04N 5/247 |
| 2019/0265712 A1* | 8/2019 | Satzoda | B60W 40/09 |
| 2019/0370578 A1* | 12/2019 | Meng | G06T 7/73 |

\* cited by examiner

FOCUS-BASED TAGGING OF SENSOR DATA

BACKGROUND

Field of the Invention

This invention relates to capturing of driver behavior.

Background of the Invention

Autonomous vehicles are an area of intense research and development. The controller of an autonomous vehicle typically receives outputs of various sensors such as cameras, RADAR sensors, LIDAR sensors, or the like. These outputs are then processed to identify road surfaces, lane boundaries, other vehicles, pedestrians, and potential obstacles. This typically requires processing a large amount of data in a very short amount of time in order to properly react to changing conditions.

The system and method disclosed herein provides an improved approach for training a machine learning model for controlling an autonomous vehicle.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings, in which.

DETAILED DESCRIPTION

Figure 1A:
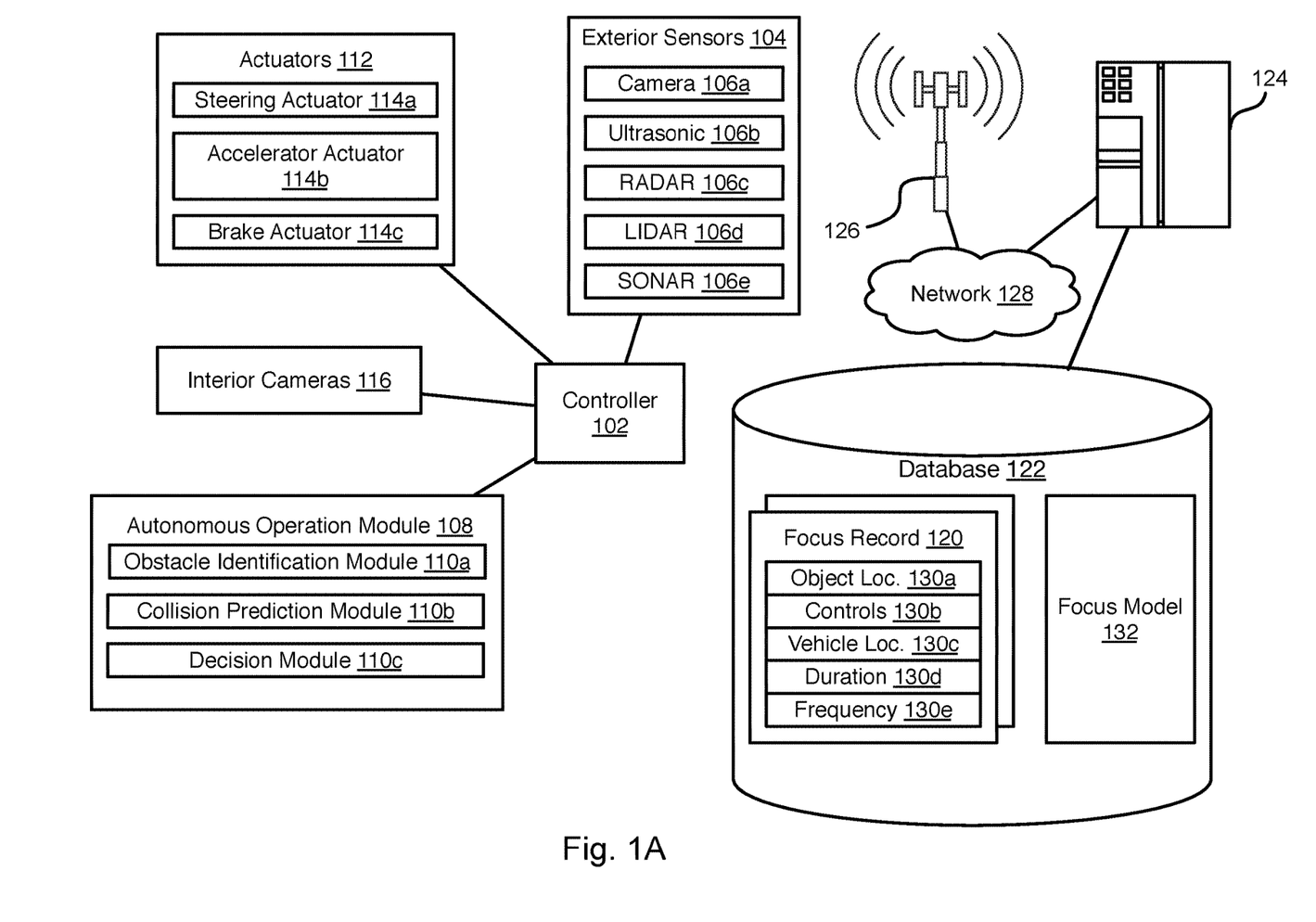
FIG. 1A is a schematic block diagram of components implementing a vehicle in accordance with an embodiment of the present invention.
Figure 1B:
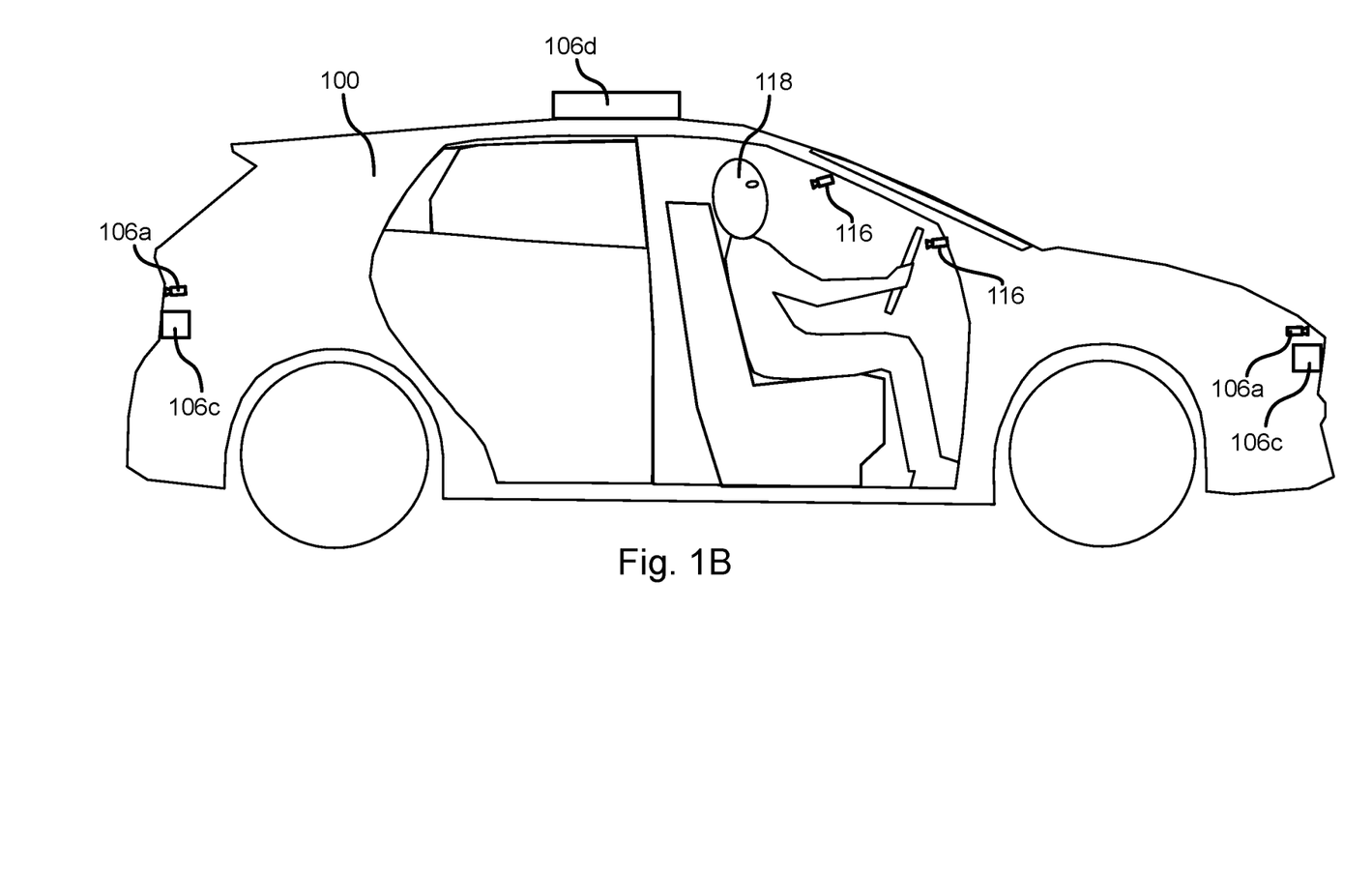
FIG. 1B is a schematic block diagram of a vehicle in accordance with an embodiment of the present invention.

Referring to FIGS. 1A and 1B, a vehicle 100 (see FIG. 1B) may include any vehicle known in the art. The vehicle 100 may have all of the structures and features of any vehicle known in the art including, wheels, a drive train coupled to the wheels, an engine coupled to the drive train, a steering system, a braking system, and other systems known in the art to be included in a vehicle.

As discussed in greater detail herein, a controller 102 mounted in the vehicle 100 may perform one or both of (a) collecting data for focus records as described herein and (b) autonomous navigation and collision avoidance. The controller 102 may receive one or more outputs from one or more exterior sensors 104. For example, one or more cameras 106a may be mounted to the vehicle 100 and output image streams received to the controller 102. In some embodiments, the exterior sensors 104 combined provide a 360 degree view around the vehicle 100. In other embodiments, a smaller viewing angle may be achieved by the exterior sensors 104, such as an angle between 180 and 270 degrees.

The exterior sensors 104 may include sensors such as an ultrasonic sensor 106b, a RADAR (Radio Detection and Ranging) sensor 106c, a LIDAR (Light Detection and Ranging) sensor 106d, a SONAR (Sound Navigation and Ranging) sensor 106e, and the like.

The controller 102 may execute an autonomous operation module 108 that receives the outputs of the exterior sensors 104. The autonomous operation module 108 may include an obstacle identification module 110a, a collision prediction module 110b, and a decision module 110c. The obstacle identification module 110a analyzes the outputs of the exterior sensors 104 and identifies potential obstacles, including people, animals, vehicles, buildings, curbs, and other objects and structures. In particular, the obstacle identification module 110a may identify vehicle images in the sensor outputs.

The collision prediction module 110b predicts which obstacle images are likely to collide with the vehicle 100 based on its current trajectory or current intended path. The collision prediction module 110b may evaluate the likelihood of collision with objects identified by the obstacle identification module 110a. The decision module 110c may make a decision to stop, accelerate, turn, etc. in order to avoid obstacles. The manner in which the collision prediction module 110b predicts potential collisions and the manner in which the decision module 110c takes action to avoid potential collisions may be according to any method or system known in the art of autonomous vehicles.

The decision module 110c may control the trajectory of the vehicle by actuating one or more actuators 112 controlling the direction and speed of the vehicle 100. For example, the actuators 112 may include a steering actuator 114a, an accelerator actuator 114b, and a brake actuator 114c. The configuration of the actuators 114a-114c may be according to any implementation of such actuators known in the art of autonomous vehicles.

In embodiments disclosed herein, the autonomous operation module 108 may perform autonomous navigation to a specified location, autonomous parking, and other automated driving activities known in the art.

The controller 102 may further be coupled to one or more interior cameras 116 having an interior of the vehicle 100 in the fields of view thereof. In particular, the one or more interior cameras 116 may have a face of a driver 118 in the fields of view thereof (see FIG. 1B). In particular, multiple cameras 116 may enable determination of the three dimensional location of the passenger's eyes, particularly the pupil thereof in order to determine a gaze direction of the passenger 118. Note that various approaches are known in the art for determining the gaze of an individual. Accordingly, the cameras 116, their positioning, and logic used to determine the gaze direction of the individual may be according to any of these prior approaches. For example, modern computer vision techniques such as neural networks and optical tracking may be used to estimate the driver's attention point and identify objects viewed by the driver in a three-dimensional scene.

As described below, the gaze direction as detected using the interior cameras 116 and features detected using the exterior sensors 104 may be used to create focus records 120 that may be stored in a database 122. For example, the controller 102 may be in data communication with a server system 124. The controller 102 may communicate with the server system 124 by way of a cellular data antenna 126 coupled to a network 128 to which the server system 124 is also connected. The data in a focus record 120 may be assembled in the focus record 120 by the controller 102 or by the server system 124. For example, the controller 102 may transmit gaze tracking data and output of sensors 104 to the server system 124, which will then assemble focus records 120 as described herein below (see discussion of FIGS. 3 and 4).

In some embodiments, a non-autonomous vehicle may be used for capturing data for inclusion in focus records 120 according to the method disclosed herein. Accordingly, the interior cameras 116 may be used whereas the actuators 112 and autonomous operation module 108 may be omitted. In other embodiments, actuators 112 and the autonomous operation module 108 may be used in to provide accident avoidance assistance rather than full autonomous operation. Likewise, exterior sensors 104 may be omitted in a human operated vehicle for capturing data for populating focus records 120 according to the methods disclosed herein in order. In other embodiments, some or all of the exterior sensors 104 are included to provide accident avoidance assistance. For autonomous vehicles having a control algorithm trained using the focus records 120 according to the methods disclosed herein, the interior cameras 116 may be omitted.

The focus records 120 include data describing a driver's gaze direction at a particular moment in time and objects determined to be viewed by the driver at that moment. Accordingly, focus records 120 may be created for each object at which the driver is determined to direct the driver's gaze. A single focus record 120 may represent a period of time during which the driver gazed at the object or may represent a single time step during which the driver's gaze was directed at the object such that each focus record 120 represents viewing of an object during a single time step, where the time step is a period at which the driver's gaze is evaluated to determine objects viewed by the driver.

A focus record 120 may include some or all of a location 130a of an object intersected by the driver's gaze direction at the moment in time, controls 130b executed or estimated to be executed by the driver in a time window including the moment in time, a location 130c of the driver's vehicle measured closest to the moment in time, a duration 130d of time the driver's gaze was directed at the object and a frequency 130e with which the driver's gaze was directed at the object.

The focus records 120 may be used for various purposes as discussed herein. One particularly useful application is to train a focus model 132 to determine what region of the field of view of sensors 104 of an autonomous vehicle should be prioritized for identification of potential hazards. The focus model 132 may be a machine learning model trained using the focus model 132.

Processing an entire scene from three-dimensional or two-dimensional sensors is computationally expensive and time intensive. By training the focus model 132 to focus on areas of particular importance, the amount of computation and delay required to identify potential hazards are reduced.

Prior approaches have attempted to use deep learning with RCNN (region-based convolution neural network) and Fast-RCNN. However, these networks tend to use a region proposal to first select regions of interest before performing object detection. However, identifying these regions is an intermediate step and prior approaches lack feedback to the learning algorithm for identification of these regions.

Figure 2:
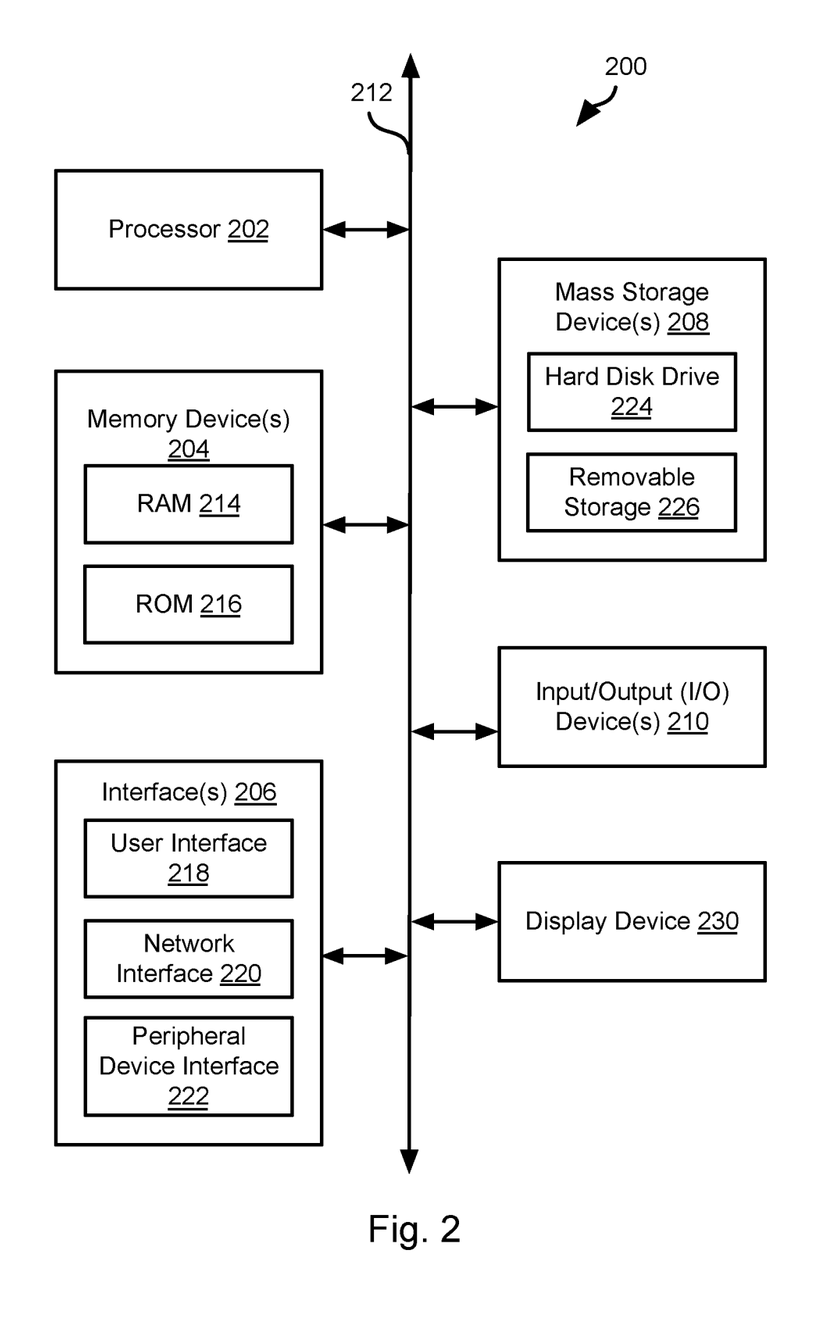
FIG. 2 is a schematic block diagram of an example computing device suitable for implementing methods in accordance with embodiments of the invention.

FIG. 2 is a block diagram illustrating an example computing device 200. Computing device 200 may be used to perform various procedures, such as those discussed herein. The controller 102 and server system 124 may have some or all of the attributes of the computing device 200.

Computing device 200 includes one or more processor(s) 202, one or more memory device(s) 204, one or more interface(s) 206, one or more mass storage device(s) 208, one or more Input/Output (I/O) device(s) 210, and a display device 230 all of which are coupled to a bus 212. Processor(s) 202 include one or more processors or controllers that execute instructions stored in memory device(s) 204 and/or mass storage device(s) 208. Processor(s) 202 may also include various types of computer-readable media, such as cache memory.

Memory device(s) 204 include various computer-readable media, such as volatile memory (e.g., random access memory (RAM) 214) and/or nonvolatile memory (e.g., read-only memory (ROM) 216). Memory device(s) 204 may also include rewritable ROM, such as Flash memory.

Mass storage device(s) 208 include various computer readable media, such as magnetic tapes, magnetic disks, optical disks, solid-state memory (e.g., Flash memory), and so forth. As shown in FIG. 2, a particular mass storage device is a hard disk drive 224. Various drives may also be included in mass storage device(s) 208 to enable reading from and/or writing to the various computer readable media. Mass storage device(s) 208 include removable media 226 and/or non-removable media.

I/O device(s) 210 include various devices that allow data and/or other information to be input to or retrieved from computing device 200. Example I/O device(s) 210 include cursor control devices, keyboards, keypads, microphones, monitors or other display devices, speakers, printers, network interface cards, modems, lenses, CCDs or other image capture devices, and the like.

Display device 230 includes any type of device capable of displaying information to one or more users of computing device 200. Examples of display device 230 include a monitor, display terminal, video projection device, and the like.

Interface(s) 206 include various interfaces that allow computing device 200 to interact with other systems, devices, or computing environments. Example interface(s) 206 include any number of different network interfaces 220, such as interfaces to local area networks (LANs), wide area networks (WANs), wireless networks, and the Internet. Other interface(s) include user interface 218 and peripheral device interface 222. The interface(s) 206 may also include one or more peripheral interfaces such as interfaces for printers, pointing devices (mice, track pad, etc.), keyboards, and the like.

Bus 212 allows processor(s) 202, memory device(s) 204, interface(s) 206, mass storage device(s) 208, I/O device(s) 210, and display device 230 to communicate with one another, as well as other devices or components coupled to bus 212. Bus 212 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 200, and are executed by processor(s) 202. Alternatively, the systems and procedures described herein can be implemented in hardware, or a combination of hardware, software, and/or firmware. For example, one or more application specific integrated circuits (ASICs) can be programmed to carry out one or more of the systems and procedures described herein.

Figure 3:
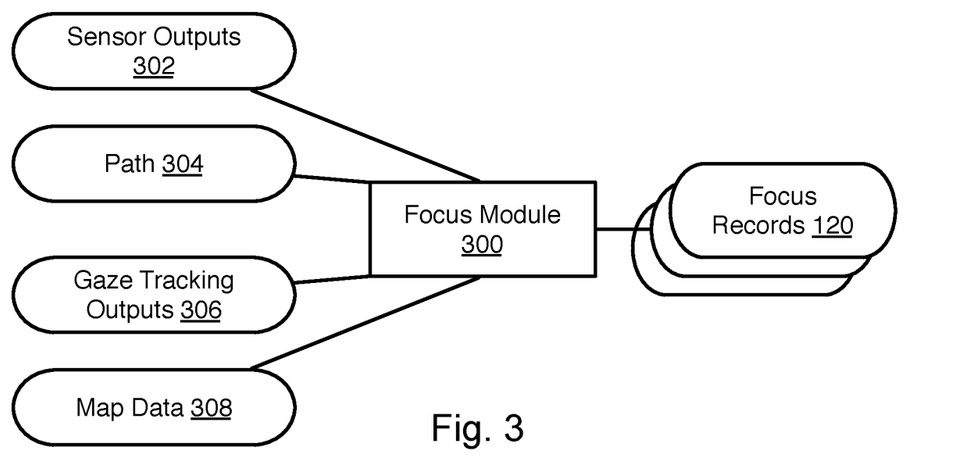
FIG. 3 is a schematic diagram of components for generating focus records in accordance with an embodiment of the present invention.

FIG. 3 illustrates generally how a focus record 120 may be created. A focus module 300 may generate the focus records 120, such as according to the method 400 of FIG. 4. The focus module 300 may be executed by the controller 102, the server system 124, or the function thereof may be distributed between the controller 102 and server system 124.

The focus module 300 takes as inputs, sensor outputs 302 from the exterior sensors 104 of the vehicle 100 and a current path 304 of the vehicle 100 during the period in which the outputs 302 were output from the sensors 104. The current path 304 may be one or both of (a) a route used by the controller 102 to provide navigation assistance and (b) a captured route traversed by the vehicle during the time period in which the sensor outputs 302 were captured.

The focus module 300 further takes as an input gaze tracking outputs 306 that include a series of data points, each data point including a location and gaze direction of the driver's eyes at a point in the time period in which the sensor outputs 302 were captured. As noted above, gaze tracking may be performed by processing the outputs of interior cameras 116 using any approach known in the art for determining the location and gaze direction of a person's eyes.

The focus module 300 may further take as input map data 308 describing a region (e.g. 50-200 foot radius) around the vehicle that was traversed during the time period in which the sensor outputs 302 were captured.

The focus module 300 outputs focus records 120 that each tag an object or region of space that was intersected by the gaze of the driver at a particular moment in time.

Figure 4:
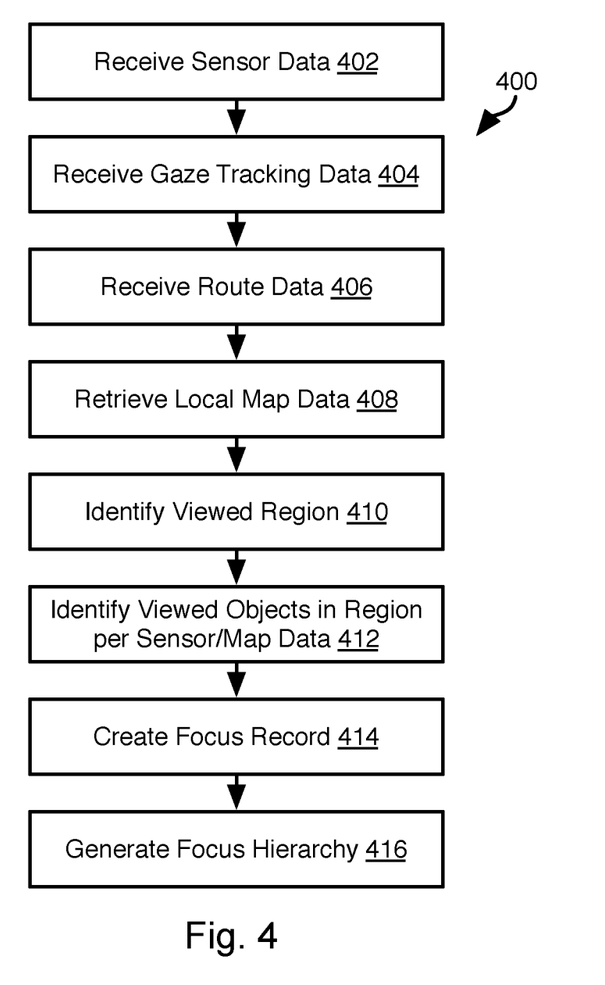
FIG. 4 is a process flow diagram of a method for generating focus records in accordance with an embodiment of the present invention.

FIG. 4 illustrates a method 400 by which focus records 120 may be created. The method 400 may be executed by the controller 102, the server system 124 or be distributed among both of these devices.

The method 400 includes receiving 402 sensor data output from the exterior sensors 104 over a period of time ("the time period"). The sensor data outputs may be embodied as a stream of readings each corresponding to a point in time in the time period. The sensor data outputs may be embodied as frames of data (camera image, radar output, LIDAR point could) corresponding to a point in the time period. For most devices, a frame of data may be detected over sampling period, such as a scanning period of a LIDAR sensor, frame rate of a video camera, or refresh rate of a RADAR. Accordingly, each frame of data for a sensor corresponds to the data collected during a sampling period, which may be sufficiently small to be treated as instantaneous for purposes of the method 400.

The method 400 may include receiving 404 gaze tracking data over the time period. For example, at a sampling period for gaze tracking, the output of the interior cameras 116 may be evaluated to determine the location and gaze direction of the driver's eyes. In some embodiments, sufficient accuracy may be achieved using only the gaze direction and using an assumed location for the driver's eyes based on typical driver height and position. Any approach known in the art for gaze tracking may be used.

The method 400 may include receiving 406 route data in the form of (a) driver controls (steering, braking, accelerating) received over the time period, (b) a route traveled by the vehicle during the time period as measured using a GPS (global positioning system) receiver or other means, or (c) a planned route used by the controller 102 to provide navigation assistance during the time period (e.g., turn-by-turn directions).

The method 400 may include receiving 408 local map data in a region surrounding the location of the vehicle 100 at various points along the route. In particular, map data for a visible region around the driver may be retrieved, such as within a 50 to 200 feet radius around the vehicle 100 at a given point of time during the time period.

Steps 410-414 of the method 400 may be performed repeatedly, each iteration being for a different time a during the time period ("the subject time"), such as points in time distributed over the time period at a sampling period that is greater than or equal to the sampling period for any of the sources of data from steps 402-406. In the description of steps 410-414, sensor data, gaze tracking data, and vehicle location data corresponding to the subject time are evaluated to generate a focus record 120 for the subject time. Due to different sampling periods and misalignment of sampling periods, reference to data from the subject time may be understood to include at least one of (a) a frame of data from each source of data corresponding to a measurement performed closest to the subject time relative to other data in the stream of data for the each source (b) a frame of data in the stream of data from the each source that immediately precedes the subject time, (c) a frame of data in the stream of data from the each source that immediately follows the subject time, (d) an interpolation of frames of data from the each source that immediately follow and immediately precede the subject time.

The method 400 may include identifying 410 a region in space viewed by the driver of the vehicle 100 at the subject time. The region in space for subject time may be determined 410 by defining a ray emanating from the location (measured or assumed) of the driver's eye and directed in the determined gaze direction of the driver at the subject time. In other embodiments, the region may be defined as a cone or pyramid centered on the ray and having a small end originating from the driver's eye.

The method 400 may include identifying 412 objects, if any, in the region from step 410 according to one or both of the sensor data from step 402 and the map data from step 408.

For example, for LIDAR data, points in the point cloud for the subject time that are within the cone or pyramid may be identified 412. In another approach, objects may be identified from the point cloud and those objects intersected by the ray may be identified 412.

In a like manner, objects and locations thereof may be identified in outputs of the cameras 116. Those objects intersected by the ray or lying within the cone or pyramid may be identified 412.

Objects identified using RADAR may be compared to the locations passed through by the ray, cone, or pyramid. Those objects intersected by the ray or overlapping the cone or pyramid may be identified 412.

For map data, road furniture (signs, traffic lights, barriers, etc.), buildings, and other features indicated by map data may be compared to the path of the ray, cone, or pyramid. Those features in the map data that are intersected by the ray or that overlap the cone or pyramid may be identified 412.

The sensor and map data used to identify 412 objects are all relatable to a location. For example, sensor data including a local two-dimensional or three-dimensional coordinate may be related to global coordinates (e.g., GPS coordinates) according to the global coordinates and orientation of the vehicle at the subject time. Accordingly, identifying 412 objects may include identifying the global position of the objects by transforming local coordinates to global coordinates.

Turning again to FIG. 4, if any objects are identified at step 412 as being intersected by the driver's gaze at the subject time, the method 400 may include creating 414 one or more focus records 120 for the subject time, each focus record 120 corresponding to an object identified at step 412. The focus record includes data describing some or all of:

A location of the vehicle at the subject time;

A maneuver (turn, stop, lane change, merging, U-turn, etc.) being executed or about to be execute by the vehicle at the subject time (e.g., the subject time precedes a maneuver indicated in the route data of step 406 by some threshold time, the vehicle location is within a threshold distance from a maneuver indicated by the route data, or the subject time occurs during execution of a maneuver indicated by the route data, etc.).

The object identified at step 412, such as in the form of the global location of the object (e.g. a centroid and/or vertices of a bounding box for the object) and a classifier of the object if possible (sign, pedestrian, building, etc.).

Map data in a region including the object, such as region including the location of the object and the location of the vehicle at the subject time.

In some embodiments, a driver may be determined to gaze at an object for multiple different times during the time period. Accordingly, a duration and frequency with which the driver gazed at the object during the time period may be calculated and stored in the focus record 120 for the object. Focus records 120 may be created for the object for each different time within the time period or may be merged into a single focus record 120 including data (vehicle location, maneuver) for each of the different times during which the driver was determined to gaze at the object during the time period.

The method 400 may further include generating a focus hierarchy 416 using focus records creating for a single driver or for many drivers. In particular, at a given location, focus records 120 around that location may be identified, i.e. that have object locations within a predefined threshold from that location.

A frequency at which that object is gazed upon by drivers when their vehicles are at the given location may be determined. For example, the frequency may be as simple as the number of focus records 120 that reference the object. Note that there may be errors in measurements of location and objects such as pedestrians will not be at the same place very time. Accordingly, focus records 120 with object locations within a predefined tolerance from one another (e.g. 2-30 cm) may be determined to correspond to the same object.

The result of step 416 is therefore a hierarchy for the given location in which objects are tagged by location and a frequency with which drivers at the given location gazed at the objects. The result is therefore a dataset that is extremely helpful in determining what regions in space are of particular concern. Alternatively, the hierarchy may be determined without reference to viewing location. Accordingly, the frequency for an object may be determined from the number of focus records 120 referencing the location of the object (within the pre-defined tolerance) regardless of the location of the vehicle indicated by the focus records.

The data set resulting from the method 400 has many applications. For example, a city planner may note that an object that should be noticed by drivers is not being looked at by drivers. Measures may therefore be taken to enhance the visibility of the object, e.g. illumination, brighter colors, larger size, etc.

Another useful application is training machine learning model to prioritize regions of space for performing hazard detection. Accordingly, for a given situation and desired maneuver, the machine learning model may be trained to focus on regions in space that are of interest to human drivers in similar circumstances. The machine learning model may then be uploaded to an autonomous vehicle and operate as trained.

For example, the machine learning model may be trained to identify those regions in space having the highest frequency according to the hierarchy and evaluate them prior to regions with lower or zero frequency according to the hierarchy, thereby reducing delay in identifying hazards. Likewise, an autonomous vehicle approaching an intersection, may evaluate regions in space having high frequency for drivers at the intersection prior to actually arriving at the intersection, thereby further reducing delay in identifying potential hazards.

Processing an entire scene from three- or two-dimensional sensor data is computationally expensive and time intensive. Human drivers tend perform this function by focusing on specific areas of interest associated with specific driving task and leaving the rest to peripheral vision at any given moment. Human drivers also tend to get better as they become more experienced.

Other approaches have tried to imitate human behavior using deep learning with R-CNN (region convolution neural network) and Fast-RCNN. These networks tend to use a region proposal to first select regions of interest before performing object detection. However, identifying these regions is an intermediate step, and prior approaches do not provide a good way to give feedback to the learning algorithm. Accordingly, the disclose system and methods provides an improved approach for training an R-CNN to identify regions of interest for a wide variety of situations.

Focus records may be used to train the machine learning according to the following approach:

1. Sensor data for a scene at a particular time, e.g. 360 degree sensor data is input to the training algorithm.
2. Focus records 120 or focus record hierarchy for the scene and particular time are provided as a desired output of the machine learning model.
3. The performance of the machine learning model is evaluated based on a predefined metric to provide feedback to the machine learning model, such as Intersection over Union (IoU) over the focus regions that were identified. In other embodiments mean Average Precision (mAP) or Average Precision (AP) may be used, such as implemented in YOLO (You Only Look Once) and similar networks. The metric could be accuracy numbers similar to that of a multi-class classification problem. One simple metric could be to capture how many of the focus regions in a scene were captured by the machine learning model and the next measure would capture the accuracy of the hierarchy of the focus regions.

In the above disclosure, reference has been made to the accompanying drawings, which form a part hereof, and in which is shown by way of illustration specific implementations in which the disclosure may be practiced. It is understood that other implementations may be utilized and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Implementations of the systems, devices, and methods disclosed herein may comprise or utilize a special purpose or general-purpose computer including computer hardware, such as, for example, one or more processors and system memory, as discussed herein. Implementations within the scope of the present disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

An implementation of the devices, systems, and methods disclosed herein may communicate over a computer network. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer-executable instructions or data structures and which can be accessed by a general purpose or special purpose computer. Combinations of the above should also be included within the scope of computer-readable media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, an in-dash vehicle computer, personal computers, desktop computers, laptop computers, message processors, handheld devices, multi-processor systems, microprocessor-based or programmable consumer electronics, network PCs, minicomputers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the description and claims to refer to particular system components. As one skilled in the art will appreciate, components may be referred to by different names. This document does not intend to distinguish between components that differ in name, but not function.

It should be noted that the sensor embodiments discussed above may comprise computer hardware, software, firmware, or any combination thereof to perform at least a portion of their functions. For example, a sensor may include computer code configured to be executed in one or more processors, and may include hardware logic/electrical circuitry controlled by the computer code. These example devices are provided herein purposes of illustration, and are not intended to be limiting. Embodiments of the present disclosure may be implemented in further types of devices, as would be known to persons skilled in the relevant art(s).

At least some embodiments of the disclosure have been directed to computer program products comprising such logic (e.g., in the form of software) stored on any computer useable medium. Such software, when executed in one or more data processing devices, causes a device to operate as described herein.

While various embodiments of the present disclosure have been described above, it should be understood that they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments, but should be defined only in accordance with the following claims and their equivalents. The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

The invention claimed is:

1. A method comprising, by a computer system:
receiving, from a vehicle controller, sensor data and captured gaze directions of a driver within a vehicle; and
for each gaze direction of at least a portion of the gaze directions:
identifying one or more features in the sensor data intersected by the each gaze direction;
creating a focus record for the one or more features, the focus record indicating driver focus on the one or more features; and
adding a driver control at a time of capture of the each gaze direction to the focus record for the one or more features;
wherein the driver control describes a driving maneuver indicated by navigation data presented by the vehicle at the time of capture of the each gaze direction.

2. The method of claim 1, wherein the sensor data include at least one of a light detection and ranging (LIDAR) point clouds, camera images, and radar sensor outputs.

3. A method comprising, by a computer system:
receiving, from a vehicle controller, sensor data and captured gaze directions of a driver within a vehicle;
for each gaze direction of at least a portion of the gaze directions:
identifying one or more features in the sensor data intersected by the each gaze direction; and
creating a focus record for the one or more features, the focus record indicating driver focus on the one or more features; and
for each gaze direction of the at least the portion of the gaze directions:
adding a location of the vehicle at a time of capture of the each gaze direction to the focus record for the one or more features.

4. A method comprising, by a computer system:
receiving, from a vehicle controller, sensor data and captured gaze directions of a driver within a vehicle; and
for each gaze direction of at least a portion of the gaze directions;
identifying one or more features in the sensor data intersected by the each gaze direction;
creating a focus record for the one or more features, the focus record indicating driver focus on the one or more features; and
adding a duration and a frequency of gazes by the driver at the one or more features to the focus record.

5. A method comprising, by a computer system:
receiving, from a vehicle controller, sensor data and captured gaze directions of a driver within a vehicle; and
for each gaze direction of at least a portion of the gaze directions;
identifying one or more features in the sensor data intersected by the each gaze direction;
creating a focus record for the one or more features, the focus record indicating driver focus on the one or more features; and
aggregating the focus records for a plurality of different drivers with respect to the one or more features to obtain a metric of relevance of the one or more features.

6. A method comprising, by a computer system:
receiving, from a vehicle controller, sensor data and captured gaze directions of a driver within a vehicle; and
for each gaze direction of at least a portion of the gaze directions;
identifying one or more features in the sensor data intersected by the each gaze direction;
creating a focus record for the one or more features, the focus record indicating driver focus on the one or more features; and
training a machine learning model according to the focus records.

7. A method comprising, by a computer system:
receiving, from a vehicle controller, sensor data and captured gaze directions of a driver within a vehicle; and
for each gaze direction of at least a portion of the gaze directions;
identifying one or more features in the sensor data intersected by the each gaze direction;
creating a focus record for the one or more features, the focus record indicating driver focus on the one or more features; and
training a machine learning model to determine a region of primary focus according to the focus records.

8. The method of claim 7, further comprising:
inputting the machine learning model to an autonomous vehicle; and
identifying hazards using the machine learning model by the autonomous vehicle.

9. A method comprising, by a computer system:
receiving, from a vehicle controller, sensor data and captured gaze directions of a driver within a vehicle; and
for each gaze direction of at least a portion of the gaze directions;
identifying one or more features in the sensor data intersected by the each gaze direction;
creating a focus record for the one or more features, the focus record indicating driver focus on the one or more features;
wherein receiving the sensor data comprises receiving the sensor data from sensors having a 360 degree view around the vehicle.

10. A system comprising one or more processing devices and one or more memory devices operably coupled to the one or more processing devices, the one or more memory devices storing executable code effective to cause the one or more processing devices to:
receive, from a vehicle controller of a vehicle, sensor data and captured gaze directions of a driver within the vehicle;
for each gaze direction of at least a portion of the gaze directions:
identify one or more features in the sensor data intersected by the each gaze direction;
create a focus record for the one or more features, the focus record indicating driver focus on the one or more features; and
add a driver control at a time of capture of the each gaze direction to the focus record for the one or more features;
wherein the driver control describes a driving maneuver indicated by navigation data presented by the vehicle at the time of capture of the each gaze direction.

11. The system of claim 10, wherein the executable code is further effective to cause the one or more processing devices to, for each gaze direction of the at least the portion of the gaze directions:

add a location of the vehicle at a time of capture of the each gaze direction to the focus record for the one or more features.

12. The system of claim 10, wherein the executable code is further effective to cause the one or more processing devices to:
add a duration and a frequency of gazes by the driver at the one or more features to the focus record.

13. The system of claim 10, wherein the executable code is further effective to cause the one or more processing devices to:
aggregate the focus records for a plurality of different drivers with respect to the one or more features to determine a frequency of viewing for the one or more features.

14. The system of claim 10, wherein the executable code is further effective to cause the one or more processing devices to train a machine learning model according to the focus records.

15. The system of claim 10, wherein the executable code is further effective to cause the one or more processing devices to train a machine learning model using the focus records to determine a region of focus.

16. The system of claim 15, wherein the executable code is further effective to cause the one or more processing devices to input the machine learning model to an autonomous vehicle.

17. The system of claim 10, wherein the sensor data includes sensor data for sensors having a 360 degree view around the vehicle.

\* \* \* \* \*